United States Patent [19]

Folkers et al.

[11] Patent Number: 5,082,650
[45] Date of Patent: Jan. 21, 1992

[54] AMELIORATION OF REDUCTIONS OF COENZYME $Q_{10}$ IN CARDIOMYOPATHY PATIENTS RECEIVING LOVASTATIN

[76] Inventors: Karl A. Folkers, 6406 Mesa Dr., Austin, Tex. 78731; Per H. Langsjoen, 3005 El Camino Dr., Temple, Tex. 76502

[21] Appl. No.: 404,228

[22] Filed: Sep. 7, 1989

[51] Int. Cl.$^5$ .................. A61K 45/00; A61K 31/405; A61K 31/35; A61K 31/12
[52] U.S. Cl. ...................................... 424/10; 514/415; 514/460; 514/690; 514/922
[58] Field of Search ................ 424/94.1, 10; 514/415, 514/460, 510, 689

[56] References Cited

U.S. PATENT DOCUMENTS 4,929,437 5/1990 Tobert .................................. 514/415
4,933,165 6/1990 Brown .................................. 514/415

OTHER PUBLICATIONS

Alberts, et al. (1980), Proc. Natl. Acad. Sci. U.S.A., 77(7):3957-61.
Merck, Sharp and Dohme, publishers (1988), Product Monograph of Mevacor® (Lovastatin/MSD), pp. 1-77.
Dr. Emile G. Bliznakov and Gerald L. Hunt, The Miracle Nutrient Coenzyme $Q_{10}$, Bantam Books, New York, New York, 1986, pp. 65-104 and pp. 220-232.

*Primary Examiner*—Douglas W. Robinson
*Assistant Examiner*—Jean C. Witz
*Attorney, Agent, or Firm*—Arnold, White and Durkee

[57] ABSTRACT

The present invention comprises the serious side effect of mevinolin to depress body levels of coenzyme $Q_{10}$ and to correspondingly depress cardiac function and the circumvention of this side effect by the clinical administration of a formulation of coenzyme $Q_{10}$ concommitantly with the administration of the mevinolin.

1 Claim, No Drawings

AMELIORATION OF REDUCTIONS OF COENZYME Q₁₀ IN CARDIOMYOPATHY PATIENTS RECEIVING LOVASTATIN

BACKGROUND OF THE INVENTION

This invention relates to a newly discovered reduction in levels of coenzyme $Q_{10}$ in human subjects which is a side effect from the administration of MEVACOR (lovastatin). The reduction of tissue levels of coenzyme $Q_{10}$ by oral MEVACOR can in turn cause an increase in cardiac dysfunction, and for patients with advanced cardiac disease, this added dysfunction can be life-threatening. Also, a reduction in levels of $CoQ_{10}$ in human subjects by MEVACOR can depress other essential functions in the human body such as the immune function which can also be very clinically serious and even life-threatening, particularly for any cancer patient.

Coronary artery disease is the major cause of death in Western countries. Hypercholesterolemia is known to be a primary risk factor for death from coronary artery disease. It is known that 50% or more of the total body cholesterol in humans is derived from intrinsic biosynthesis. It is also known that a rate-limiting step of major significance in the biosynthesis of cholesterol is at the level of the enzyme known as 3-hydroxy-3-methylglutaryl-coenzyme A reductase or HMG-CoA reductase. This enzyme then was logical for inhibition to reduce the intrinsic biosynthesis of cholesterol toward reducing the risk factor of hypercholesterolemia and coronary artery death.

Alberts et al. (*Proc. Natl. Acad. Sci. USA*, Vol., 77, No. 7, pp. 3957-3961, July 1980) described the isolation, structure and biochemical properties of an active inhibitor of HGM-CoA reductase which they named mevinolin. The scientific trivial name, mevinolin, introduced in 1980, corresponds to the subsequent trademark name, MEVACOR ®, (lovastatin/MSD). This chemical substance is 1,2,6,7,8,8a-hexahydro-$\beta$,$\delta$-dihydroxy-2,6-dimethyl-8-(2-methyl-1-oxobutoxy)-1-naphthaleneheptanoic acid$\delta$-lactone. The chemical structure of MEVACOR is:

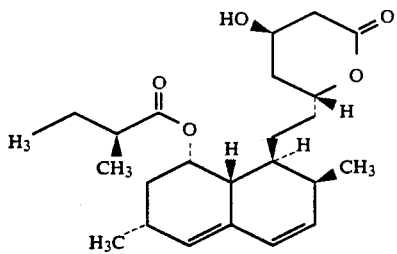

The Product Monograph on MEVACOR by Merck, Sharp and Dohme (issued May 1988, DC 7489503) states that MEVACOR is highly effective in the treatment of hypercholesterolemia. Further, at maximum doses, MEVACOR produced a mean reduction of LDL cholesterol of 39% in two large multicenter control studies. In general, MEVACOR was found to be well-tolerated in continuing extensive clinical trials as based on data from studies worldwide. However, approximately 2% of patients were discontinued from therapy due to drug-related adverse effects in all clinical studies. The most frequently reported adverse experiences were: headache (9.3%), flatus (6.4%), abdominal pain/cramps (5.7%), diarrhea (5.5%) and rash/pruritus (5.2%) (page 66).

Further, (page 66) the adverse experiences on treating patients with MEVACOR in controlled clinical studies were GASTROINTESTINAL (constipation, diarrhea, dyspepsia, flatus, abdominal pain/cramps, heartburn and nausea); and MUSCULOSKELETAL (muscle cramps and myalgia); and NERVOUS SYSTEM/PSYCHIATRIC (dizziness, headache); SKIN (rash/pruritus); and SPECIAL SENSES (blurred vision and dysgeusia). Although some of these adverse experiences were also recorded when a placebo was administered, MEVACOR did produce such adverse experiences without doubt.

Also, (page 67), liver dysfunction from MEVACOR can occur and approximately 0.5% of patients in clinical trials developed a myopathy.

Also, (page 68), there were eye dysfunctions indicated by a high prevalence of baseline lenticular opacities and during clinical trials, the appearance of new opacities was noted. The causal relationship of MEVACOR to these opacities was not established. Of 431 patients, 34 had opacities at the final examination which occurred during 5-15 months after initiating therapy with MEVACOR. However, existing opacities did not appear to increase.

In summary of the tolerability or the side effects from the clinical administration of MEVACOR, this drug does have a variety of definite side effects some of which have justified discontinuation of therapy with MEVACOR, particularly liver dysfunction.

SUMMARY OF THE INVENTION

The present invention comprises the heretofore overlooked and very serious side effect of MEVACOR to depress body levels of coenzyme $Q_{10}$ and to depress correspondingly cardiac function or the pumping of blood by the heart throughout the body, and the circumvention of this death-threatening side effect by the clinical administration of a formulation of coenzyme $Q_{10}$ either (1) concomitantly with MEVACOR or (2) by independent formulations of MEVACOR and coenzyme $Q_{10}$ by an appropriate dosage schedule for MEVACOR and coenzyme $Q_{10}$ ($CoQ_{10}$).

The depressed cardiac function which can be caused by MEVACOR is associated with the discovered reduction in blood levels of coenzyme $Q_{10}$ ($CoQ_{10}$) during the clinical administration of MEVACOR.

Crane reviewed the physiological function of coenzyme $Q_{10}$ (*Biomedical and Clinical Aspects of Coenzyme Q*, Vol. 5, 1986, eds., K. Folkers & Y. Yamamura, Amsterdam, The Netherlands: Elsevier Science Publishers B.V., pp. 3-14).

$CoQ_{10}$ is a redox coenzyme of the respiratory chain including mechanisms of oxidative phosphorylation. These mechanisms have been known as "bioenergetics" and support life functions including the cardiac function or the pumping of blood by the heart. $CoQ_{10}$ is a coenzyme for the mitochondrial enzymes: NADH:$CoQ_{10}$ reductase, succinate:$CoQ_{10}$ reductase, electron transfer flavoprotein:$CoQ_{10}$ reductase, reduced $CoQ_{10}$: cytochrome C reductase. The energy coupling roles of $CoQ_{10}$, and the apparent antioxidant activity of $CoQ_{10}$, are the specific reactions which are important to maintain metabolic functions of organs such as cardiac function. Any pharmacological treatment, any drug treatment such as the clinical administration of MEVACOR to reduce hypercholesterolemia which reduces blood levels of CoQ$_{10}$ and thereby reduces the energy-coupling and other roles of CoQ$_{10}$ can be clinically detrimental such as to cardiac function and even life itself.

CASE SUMMARIES AND DATA

Case Data of Patient H.V.

Patient H.V., 55 years, was a white male with ischemic cardiomyopathy, and in Class III by the New York Heart Association. The classification of functional capacity in widest use was arrived at by the New York Heart Association and is as follows:
Class I: Ordinary activity causes no discomfort.
Class II: Ordinary activity causes symptoms.
Class III: Minimal activity causes distress.
Class IV: Patient is symptomatic at rest.

He was orally treated with 100 mg of coenzyme Q$_{10}$ daily beginning in May, 1984. His control blood level of CoQ$_{10}$ was 0.67 µg/ml and his control ejection fraction (E.F.) was 60%. One month later (6/84), the CoQ$_{10}$ blood level had increased to 1.73 µg/ml and the ejection fraction had increased to 74%. The following data on blood levels of CoQ$_{10}$ and on the ejection fractions from 7/84 to 9/87 show that oral and daily therapy with CoQ$_{10}$ maintained a therapeutic level of CoQ$_{10}$ of 1.73–2.78 µg/ml and ejection fractions of 64–70%. During these three years of therapy with CoQ$_{10}$, the classification of ischemic cardiomyopathy of this patient had decreased from Class III to Class II and the quality of life of this patient was correspondingly significantly improved. On 9/87, this patient was treated with 40 mg of MEVACOR daily and by 3/88 the patient had steadily deteriorated from a livable Class II to near Class IV which is known to be life-threatening. In this deterioration, the patient exhibited clinical decompensation and chest pain and required surgical revision of one graft. Documenting his clinical deterioration, his CoQ$_{10}$ blood level was 2.52 on 9/87 when treatment with MEVACOR was initiated and about six months later on 3/88 his blood CoQ$_{10}$ level had diminished to 1.15 µg/ml and to the very low level of 0.64 µg/ml five months later on 8/88. On this later date, the ejection fraction had diminished to 54%. During the surgical period, it was not feasible to orally administer CoQ$_{10}$ for three weeks, but administration of CoQ$_{10}$ was resumed at 166 mg per day on 8/88. One month later, the blood CoQ$_{10}$ level had increased to 1.39 µg/ml (on 9/88) and was stabilized at 1.55 on 11/88 and 1.66 µg/ml on 4/89. The administration of MEVACOR was reduced from 40 mg per day to 20 mg per day on 11/88. The depressed CoQ$_{10}$ blood levels from the administration of MEVACOR, which in conjunction with the reduction of the dosage of MEVACOR from 40 mg to 20 mg daily and an increase in the dosage of CoQ$_{10}$ allowed the cardiac stabilization of this patient with acceptable blood levels of CoQ$_{10}$ and that of the ejection fractions.

CASE SUMMARY ON PATIENT H. V.
1) H. V. 55 W/M Ischemic Cardiomyopathy. Class III to Class II.

| | Date | | | | | | | |
|---|---|---|---|---|---|---|---|---|
| | 5/84 | 6/84 | 7/84 | 10/84 | 5/85 | 11/85 | 5/86 | 9/86 |
| CoQ$_{10}$ | 0.67 | 1.73 | 1.32 | 1.81 | 2.41 | 2.13 | 2.57 | 2.12 |
| E.F. | 60 | 74 | 69 | 66 | 70 | 64 | 68 | 72 |

| | Date | | | | | | |
|---|---|---|---|---|---|---|---|
| | 3/87 | 9/87 | 3/88 | 8/88 | 9/88 | 11/88 | 4/89 |
| CoQ$_{10}$ | 2.78 | 2.52 | 1.15 | 0.64 | 1.39 | 1.55 | 1.66 |
| E.F. | 70 | 70* | 76** | 54*** | 63 | 74**** | 71 |

*MEVACOR 40 mgm/day added.
**Patient rapidly deteriorated from Class II to near Class IV with decompensation and chest pain. Had surgical revision of one graft. Missed 3 weeks of CoQ$_{10}$ during surgical period.
***CoQ$_{10}$ resumed at 166 mgm/day
****MEVACOR reduced to 20 mgm daily In summary, patient H.V. was showing blood levels of CoQ$_{10}$ of 2.57–2.52 µg/ml between 5/86 and 9/87, on treatment with 100 mg of CoQ$_{10}$ orally and daily, and ejection fractions of 68–70, during this same period. After initiating treatment with MEVACOR on 9/87, the blood level of CoQ$_{10}$ declined within 6 months from 2.52 to 1.15 µg/ml and then in five more months declined to 0.64 µg/ml. On this latter date, a dosage of CoQ$_{10}$ was resumed at 166 mg/day and blood levels increased to 1.39–1.66 µg/ml between 9/88 and 4/89 and noticeably never reached levels of 2.5 µg/ml.

Although the dosage of MEVACOR was reduced on 11/88 from 40 to 20 mg daily, the blood levels of CoQ$_{10}$ and the level of the ejection fraction remained essentially unchanged.

Clearly, the administration of MEVACOR over time significantly reduced blood levels of CoQ$_{10}$ and reduced the pumping of blood by the heart as monitored by the ejection fraction.

CASE DATA OF PATIENT B.C.

This patient, 46 years, was a white male with dilated cardiomyopathy. He was in Class III by the New York Heart Association and his control blood level of CoQ$_{10}$ was 0.78 µg/ml and his control ejection fraction was 62% on 10/84. According to the following data, his blood levels of CoQ$_{10}$ increased to the range of 1.79–2.31 µg/ml and his ejection fraction increased to the range of 68–71%. During this two-year and four-month period, his cardiac function and his quality of life had improved from Class III to Class I and his cardiac function stabilized at a clinically reasonable level.

Then on 4/87, he was given 20 mg daily of MEVACOR and 6–18 months later, his CoQ$_{10}$ blood levels had steadily declined from 2.29 to 1.82 to 1.50 to 1.12 µg/ml. On 10/88, the administration of MEVACOR was terminated, and on 3/89 his CoQ$_{10}$ blood level had increased to 1.87 µg/ml.

CASE SUMMARY ON PATIENT B. C.
B. C. 46 W/M Dilated Cardiomyopathy 51. Class III to Class I.

| | Date | | | | | | | | | | |
|---|---|---|---|---|---|---|---|---|---|---|---|
| | 10/84 | 12/84 | 3/85 | 9/85 | 3/86 | 10/86 | 4/87 | 10/87 | 4/88 | 10/88 | 3/89 |
| CoQ$_{10}$ | .78 | 1.96 | 1.79 | 2.31 | 2.09 | 1.86 | 2.29 | 1.82 | 1.50 | 1.12 | 1.87 |
| E.F. | 62 | 69 | 70 | 71 | 71 | 71 | 68* | 70 | 68 | 71** | 63 |

*MEVACOR 20 mgm/day
**MEVACOR stopped

These data on patient B.C. clearly show reduction of blood levels of CoQ$_{10}$ over time from the administration of MEVACOR and the increase in blood levels of CoQ$_{10}$ when the administration of MEVACOR was terminated.

CASE DATA ON PATIENT S.F.

This patient was a white female of 43 years (now 46) and had dilated cardiomyopathy and was in severe Class IV when treatment with CoQ$_{10}$ was initiated.

Between 3/86 and 9/87, her blood CoQ$_{10}$ levels ranged from 1.68–3.22 μg/ml and her ejection fraction ranged from 52–60%. Her clinical status improved to Class III.

On 9/87, treatment with 20 mg of MEVACOR was initiated and by 3/88 her cardiac condition had significantly deteriorated to a severe Class IV and the patient was referred for a heart transplant.

On 3/88, her dosage of CoQ$_{10}$ was increased to 200 mg/daily and blood levels of CoQ$_{10}$ increased to the range of 4.24–5.43 between 10/88 and 4/89, and on this later date, her cardiac condition had significantly improved from Class IV to Class III, which is explained on the basis of the increase in the daily dosage of CoQ$_{10}$ to 200 mg daily and in the presence of continuing daily treatment of 20 mg of MEVACOR.

| CASE SUMMARY ON PATIENT S. F. S. F. 46 W/F Dilated Cardiomyopathy. Class IV–Class III | | | | | | | |
|---|---|---|---|---|---|---|---|
| | Date | | | | | | |
| | 3/86 | 9/86 | 3/87 | 9/87 | 3/88 | 10/88 | 4/89 |
| CoQ$_{10}$ | 1.68 | 3.25 | 4.26 | 3.22 | 2.57 | 4.24 | 5.43 |
| E.F. | 52 | 55 | 54 | 60* | 48** | 66*** | 75**** |

*MEVACOR 20 mgm added
**Rapid deterioration to severe Class IV. Referred for transplant. CoQ$_{10}$ increased to 200 mgm/day.
****Improved to Class III This patient was initially in Class IV and her cardiomyopathy improved to Class III after treatment with CoQ$_{10}$. After treatment with MEVACOR was added, she deteriorated from Class III to severe Class IV and so rapidly that she was referred for a cardiac transplant. Then her dosage of CoQ$_{10}$ was increased from 100 to 200 mg daily and resulted in improved ejection fraction and reclassification to Class III.

CASE DATA ON PATIENT M.O.

This patient was a 72-year old white female in Class III with dilated cardiomyopathy.

On 3/86, her blood level of CoQ$_{10}$ was 0.79 μg/ml and her ejection fraction was 58%. On 100 mg of CoQ$_{10}$ daily, her CoQ$_{10}$ blood level after 3 months was 1.21 μg/ml and ejection fraction remained at 58%. On 9/86, the CoQ$_{10}$ dosage was increased to 133 mg daily and during 3/87–9/87 her CoQ$_{10}$ blood levels were 1.70 and 2.23 μg/ml with an improved ejection fraction of 61–63%.

On 9/87, the administration of MEVACOR was initiated at 20 mg daily and by 3/88 the CoQ$_{10}$ blood level had decreased to 0.99 μg/ml and ejection fraction was 65%. On 8/88, her blood level of CoQ$_{10}$ was 1.68 μg/ml and on 2/89, it was 1.00 μg/ml. On the higher dosage of CoQ$_{10}$, her ejection fraction ranged from 76–79%.

Again, the administration of MEVACOR had decreased the blood level CoQ$_{10}$ during six months.

| CASE SUMMARY OF M. O. M. O. 72 W/F Dilated Cardiomyopathy. Class III to Class II. | | | | | | | |
|---|---|---|---|---|---|---|---|
| | Date | | | | | | |
| | 3/86 | 6/86 | 9/86 | 3/87 | 9/87 | 3/88 | 8/88 | 2/89 |
| CoQ$_{10}$ | 0.79 | 1.21 | 1.21 | 1.70 | 2.23 | 0.99 | 1.68 | 1.00 |
| E.F. (%) | 58 | 58 | 64* | 63 | 61** | 65 | 76 | 79*** |

*CoQ$_{10}$ increased to 133 mgm/day
**MEVACOR 40 mgm/day
***CoQ$_{10}$ increased to 166 mgm/day When this 72-year old female with Class III cardiomyopathy was treated with CoQ$_{10}$, her cardiomyopathy improved to Class II in 12 months. On administration of MEVACOR, her CoQ$_{10}$ blood level significantly diminished and with deterioration in clinical status but not in ejection fraction.

CASE DATA ON PATIENT J.G.

This patient was a 66-year old white male (now 67) with ischemic cardiomyopathy and who was initially in Class I when MEVACOR at a daily dosage of 20 mg was initiated. On that date, 1/88, the ejection fraction was 85%. One year later, the blood level of CoQ$_{10}$ was 0.61 μg/ml and the ejection fraction had decreased to 52% at which time 100 mg of CoQ$_{10}$ daily was initiated because the cardiomyopathy had definitely worsened to Class III. By 3/89, the CoQ$_{10}$ level was 1.02 μg/ml and the ejection fraction was 61% and the dosage of CoQ$_{10}$ was increased to 133 mg daily.

For this patient, J.G., MEVACOR significantly decreased the ejection fraction over a year and increased the severity of ischemic cardiomyopathy from Class I to Class III. The administration of CoQ$_{10}$ had increased within two months the blood CoQ$_{10}$ level to offset the depression of this blood level from MEVACOR.

| CASE SUMMARY ON J. G. J. G. 67 W/M Ischemic Cardiomyopathy. Class I–III | | | | |
|---|---|---|---|---|
| | Date | | | |
| | 1/88 | 1/89 | 3/89 | 6/89 |
| CoQ$_{10}$ | – | 0.61 | 1.02 | 1.01 |
| E.F. | 85* | 52** | 61*** | 66 |

*MEVACOR 20 mgm/day
**CoQ$_{10}$ 100 mgm/day
***CoQ$_{10}$ 133 mgm/day

Patient J.G., 67 yrs. was post-op bypass because of ischemic heart disease in Class I. He was placed on MEVACOR on 5/88 because of elevated blood lipids. However, there was progressive symptoms of weakness and dyspnea on activities and his cardiac status had declined from Class I to Class III by 1/89 with a corresponding decrease in ejection fraction. When CoQ$_{10}$ was given at 100 mg daily, his CoQ$_{10}$ blood level increased from 0.61 to 1.02 μg/ml and his ejection fraction increased from 52 to 61%, on 1/89 and 3/89, respectively. When his CoQ$_{10}$ dosage was increased from 100 to 133 mg daily on 3/89, the ejection fraction increased to 66% by 6/89.

CONCLUSION

Patients B.C. and M.O. revealed quite rapid cardiovascular deterioration on MEVACOR. This deterioration was sufficiently progressive and severe that neither patient was expected to live very long. For both of these patients, their clinical course was significantly improved when the dosage of CoQ$_{10}$ was increased.

THERAPY OF CARDIOMYOPATHY WITH COENZYME $Q_{10}$ IN THE ABSENCE OF MEVACOR

Langsjoen et al. (*Klinische Wochenschrift*, 1988, 66:583-590) reported in 1988 on the effective and safe therapy with coenzyme $Q_{10}$ for cardiomyopathy. Patients with the lowest ejection fractions (approximately 10-30%) showed the highest increases (115Δ%-210Δ%) and those with higher ejection fractions (50%-80%) showed increases of approximately 10Δ%-25Δ% on therapy. By functional classification, 17/21 in Class IV, 52/62 in Class III and 4/5 in Class II improved to lower Classes. Clinical responses were variable and were presumed to be based on mechanisms of DNA-RNA protein synthesis of apoenzymes which restored levels of CoQ10 enzymes in a deficiency state. 10/21 (48%) of patients in Class IV, 26/62 (42%) in Class III, and 2/5 (40%) in Class II had exceptionally low control blood levels of $CoQ_{10}$. Clinical responses on therapy with $CoQ_{10}$ appear maximal with blood levels of approximately 2.5 μg/ml and higher during therapy.

The administration of MEVACOR to such patients with cardiomyopathy which depressed blood levels of $CoQ_{10}$ would definitely be deleterious to cardiac function, and would be increasingly life-threatening in relationship to the increasing severity of the cardiac disease.

Langsjoen et al. (*The American Journal of Cardiology*, submitted in May 1989) summarized the long-term efficacy and safety of coenzyme $Q_{10}$ to treat cardiomyopathy. Their study involved the adminstration of doses of 100 mg of $CoQ_{10}$ daily to 143 patients with cardiomyopathy for up to six years for up to a total of 402 patient years of exposure. The generally low control blood levels of $CoQ_{10}$ were corrected well into the normal range and remained stable thereafter. Myocardial contractility, as measured by ejection fraction, was significantly improved in 85% of all patients and this improvement was sustained for up to six years and correlated well with improvement in the quality of life. Clinical improvements of 1 or 2 NYHA Classes were recorded in 85% of all cases. Survival figures were highly encouraging. $CoQ_{10}$ was proven efficacious and safe for the treatment of cardiomyopathy over a six-year period. It was evident that abnormalities in intracellular bioenergetics are likely factors in the enigma of myocardial failure and present the unique medical opportunity to correct this serious health problem from an entirely new biochemical approach. In this study, over six years, there were no significant side reactions.

THE DISCOVERY

It is discovered from the data herein that the administration of MEVACOR to patients having from mild to severe cardiomyopathy depresses $CoQ_{10}$ blood levels, definitely is deleterious to cardiac function, and is life-threatening.

DESCRIPTION OF THE PREFERRED EMBODIMENT

MEVACOR is presently administered to countless patients all over the United States having hypercholesterolemia. The data herein reveal that oral MEVACOR causes a reduction in the blood levels of coenzyme $Q_{10}$ in typical and symbolic subjects, and this reduction of $CoQ_{10}$ is definitely related to a decrease in ejection fraction or an increase in cardiac dysfunction. It is also clearly evident scientifically that there would definitely be a decrease in immune function, as well as other metabolic functions which are intrinsically dependent upon adequate tissue levels of coenzyme $Q_{10}$.

Many of the patients presently being treated in the U.S. with MEVACOR have mild to severe stages of cardiomyopathy, dilated or ischemic, and ranging from mild cases to and including Class I to severe patients up to and including Class III and IV.

Clinically, it is presently common for MEVACOR to be administered to patients having hypercholesterolemia over prolonged periods of time ranging from weeks to months to years and for the longer periods to prophylactically maintain low levels of cholesterol. This prolonged administration of MEVACOR to a variety of patients definitely indicates that countless such patients will have depressed tissue levels of $CoQ_{10}$ and correspondingly depressed metabolic functions such as cardiac, immune, and others.

Patients presently receiving MEVACOR have a great range of age, doubtless from the 20's to the 80's or even older. Such patients of such variable age will necessarily have variable levels of $CoQ_{10}$ according to present biochemistry, and thus their variable low tissue levels of $CoQ_{10}$ will bear some relationship to degrees of cardiac dysfunction, immunodysfunction, etc.

The five symbolic case summaries and data described herein clearly illustrate that the administration of MEVACOR to human subjects having from mild (Class I) to severe (Class IV) stages of cardiomyopathy can result in variable periods of time in reductions of $CoQ_{10}$ blood levels and such reductions are independently known to be correlated with degrees of cardiac dysfunction or cardiomyopathy, including both dilated and ischemic categories.

Of these five symbolic case summaries, MEVACOR caused such significant deterioration of cardiac function that a patient initially in Class II declined to Class IV with decompensation and chest pain which resulted in surgical revision of one graft.

In another of the five symbolic cases, MEVACOR caused such rapid deterioration to a severe Class IV from an earlier Class III state that the patient was referred for a cardiac transplant. However, increasing the oral dosage of $CoQ_{10}$ to 200 mg daily circumvented the need for a cardiac transplant and allowed the patient to improve from a severe Class IV to Class III.

These five case summaries clearly illustrate the discovered severe side effect of MEVACOR to depress $CoQ_{10}$ blood levels and to cause an increase to more severe NYHA cardiomyopathy classifications whether the initial cardiac condition before treatment with MEVACOR was Class I or Class II or Class III. This projection would be the same if the study were based on 50 cases or 100 cases or even more.

In cardiology, the treatment of patients having from mild to severe cardiomyopathy with MEVACOR which has been shown herein to depress $CoQ_{10}$ blood levels and to depress cardiac function is clinically very undesirable because the quality of cardiac function is depressed and even a life-threatening status can develop which may require surgery and even a cardiac transplant.

Changes may be made in formulations of MEVACOR and of coenzyme $Q_{10}$, and changes may be made in the dosage schedule of formulations and of the various elements, and changes may be made in the steps and procedures described herein without departing from the concept and scope of the invention as defined in the following claims.

What is claimed:

1. A method of ameliorating the reduction of coenzyme Q10 in a patient receiving mevinolin for the treatment of dilated or ischemic cardiomyopathy, said method comprising the concurrent administration of coenzyme Q10 in amounts effective to maintain clinically effective blood levels of coenzyme Q10 and mevinolin in amounts effective to produce clinically effective reductions in levels of cholesterol.

* * * * *